(12) United States Patent
Merkel

(10) Patent No.: US 7,040,168 B1
(45) Date of Patent: May 9, 2006

(54) APPARATUS FOR DETERMINING PHYSICAL PARAMETERS IN AN OBJECT USING SIMULTANEOUS MICROWAVE AND ULTRASOUND RADIATION AND MEASUREMENT

(75) Inventor: Harald Merkel, Lidome (SE)

(73) Assignee: Frigoscandia Equipment AB, Helsingborg (SE)

( * ) Notice: Subject to any disclaimer, the term of this patent is extended or adjusted under 35 U.S.C. 154(b) by 0 days.

(21) Appl. No.: 10/986,223

(22) Filed: Nov. 12, 2004

(51) Int. Cl.
*G01R 27/26* (2006.01)
*G01N 29/04* (2006.01)

(52) U.S. Cl. .................................................. 73/601
(58) Field of Classification Search ................. 73/601
See application file for complete search history.

(56) References Cited

U.S. PATENT DOCUMENTS

| | | | | |
|---|---|---|---|---|
| 3,961,199 | A | * | 6/1976 | Bronicki .................. 290/52 |
| 4,167,878 | A | * | 9/1979 | Bottcher et al. ............. 73/601 |
| 5,115,673 | A | * | 5/1992 | Kline et al. ................ 73/601 |

FOREIGN PATENT DOCUMENTS

WO  WO-2004-029600 A1  4/2004

OTHER PUBLICATIONS

Derwent Publications Ltd., London, GB; 1984-068151 & SU1019312 A (DAVY-I) DAVYDOV NV. (May 23, 1984).
Derwent Publications Ltd., London, GB; AN 1986-129887. (Oct. 15, 1985), SU 1185269A.
Derwent Publications Ltd., London, GB; AN 1994-180890 & SU944468A1 (ASRA). (Jan. 15, 1993).
Ultrasonics 2003, IEEE Symposium, Oct. 5-8, 2003, Title "Ultrasonic Thermal Imaging of Microwave Absorption", Y. Shi et al.

* cited by examiner

*Primary Examiner*—Hezron Williams
*Assistant Examiner*—Rose M. Miller
(74) *Attorney, Agent, or Firm*—Birch, Stewart, Kolasch & Birch, LLP

(57) ABSTRACT

The present invention relates to an apparatus for determining a dielectric function in an object. The apparatus includes one transmit antenna for transmitting microwave radiation through the object, and one receive antenna for receiving the transmitted microwave radiation, one ultrasound transmitter for emitting ultrasound radiation through the object to generate a density variation in the object, means to analyse the microwave radiation transmitted through the density variation to determine the acousto-electric interaction in the object, and a device to calculate the dielectric function in the object from the acousto-electric interaction. The invention also relates to a method for determining the dielectric function in an object.

15 Claims, 9 Drawing Sheets

APPARATUS FOR DETERMINING PHYSICAL PARAMETERS IN AN OBJECT USING SIMULTANEOUS MICROWAVE AND ULTRASOUND RADIATION AND MEASUREMENT

TECHNICAL FIELD

The present invention relates to an apparatus for determining physical parameters, such as temperature or density, inside an object by determining the dielectric function of the object as defined in claim 1. The invention also relates to a method for determining the dielectric function inside an object as defined in claim 10, and an apparatus for determining the local distribution of temperature in a food product as defined in claim 15.

BACKGROUND OF THE INVENTION

In order to obtain information regarding temperature, density and other interior parameters of arbitrary objects without destroying, invading or dissecting the object, radiation(s) of various types are available to provide information that allow(s) to reconstruct the desired parameters.

Choosing a specific type of radiation, there are four distinct cases that incorporate their proper implications on the choice of method of analysis. These are classified by two question areas:
- transparency of the object to the radiation chosen
- resolution in the object required with respect to the wavelength of the chosen radiation.

Case 1A (The object is transparent or weakly absorbing to the radiation used for measurement, and the resolution to be achieved is equal or smaller than a radiation wavelength).

The only source of information is obtained by probing the near field using e.g.

Atomic Force Microscopy (APM)
  reading out the force on a sub-wavelength-size stencil being positioned with high precision on the surface of a material reading out the structure on the surface of the object under test, Raster Tunnel Microscopy (RTM)
  where instead of the force one measures the tunneling current from a sub-wavelength sized probe being positioned close to the surface of the object under test generating information on the electronic state of the surface of the object, or optical Near Field Microscopy
  where electromagnetic radiation passes through microscopically small holes requiring the hole to be much smaller than a wavelength of the radiation used generating surface images of the optical properties at sub wavelength resolution on thin probes.

Impedance tomography
  Where a set of electrodes is attached to the object under test and the impedance between all the probes is measured. This method allows calculating some properties of the interior of the object under test but resolution is generally poor. This method has been used with success in differential approaches—measuring the impedance of the cardiac region prior and after medication to evaluate the influence of, e.g. anti-clogging drugs.

As a general feature, the high resolution of the methods mentioned above are not due to the intrinsic wavelength of the chosen radiation but due to another constraint (mostly mechanical as diaphragms, stencils) that provides sub-wavelength resolution. A general shortcoming is given by the thickness requirement of the object under test—the above methods generate either only surface information or interior information at a very limited depth without losing resolution.

Case 1B (The object is transparent or weakly absorbing to the radiation used for measurement, and the resolution is much larger than a radiation wavelength.)

This case is covered by all direct imaging and optical transmission methods. Using electromagnetic radiation in this regime, there are
  LIDAR
  X-ray As a means of analysis, ray tracing and one-to-one mapping methods are appropriate since scattering does not play a role—it can be assumed without loss of resolution that each pixel information taken at a given position is only affected by the object's volume located in between the radiation source and the receiver.

A recent development in this area is the passive radar where the thermal emission inherent to all bodies in the environment around a receiver is measured and imaged. This radar method does not require any transmitted signal and is therefore not traceable.

Among non-electromagnetic methods there are commercially available
  Ultrasound tomography and
  Nuclear Magnetic Resonance (NMR)

Case 2A (The object is moderately absorbing to the radiation used for measurement, and the resolution is equal or smaller than a radiation wavelength).

The fact that the object is moderately absorbing to the radiation used for measurement puts a thickness limit to the probes that can be investigated.

For this case no feasible method is available today regarding the state of the art.

Case 2B (The object is moderately absorbing to the radiation used for measurement, and the resolution is much larger than a radiation wavelength).

In this case, most radio frequency and microwave frequency applications are found (especially when the object under test is lossy and it is embedded in a non-lossy environment) and microwave tomography is available. Among these methods the most popular one is
  (active) radio detection and ranging (RADAR)
    where the signal runtime between a source and a target and back to a receiver is measured either by putting the receiver at the same place as the transmitter (monostatic radar) or by putting the receiver at a different location than the transmitter (bistatic radar) and the frequency change due to the relative velocity of the source and target are evaluated (Doppler radar).

There is thus a need to develop an apparatus for determining physical parameters, such as temperature, density, composition, for an object that is modestly absorbing to the radiation used for measurement, and where the desired resolution is much larger than a radiation wavelength.

SUMMARY OF THE INVENTION

The purpose of the present invention is to provide an apparatus for determining the dielectric function of an arbitrarily formed object.

The purpose is achieved by an apparatus according to claim 1, and a method according to claim 10, using ultrasound waves to create a controllable variation in product density. The apparatus then uses microwave radiation to read out the density variation and to relate it to a spatial distribution of the dielelectric function. This may in turn be used for determining the object's temperature, water content and density.

An advantage with the present invention is that the resolution of the spatial distribution not is limited to the microwave wavelength, but rather determined by the wavelength of the ultrasound.

Another advantage with the present invention is that a contact free measurement of physical properties, such as temperature, water content, etc, may be established applying the invention as virtual probes.

Other objects and advantages will be apparent for a skilled person from the detailed description of the invention.

DETAILED DESCRIPTION OF PREFERRED EMBODIMENTS

Figure 1:
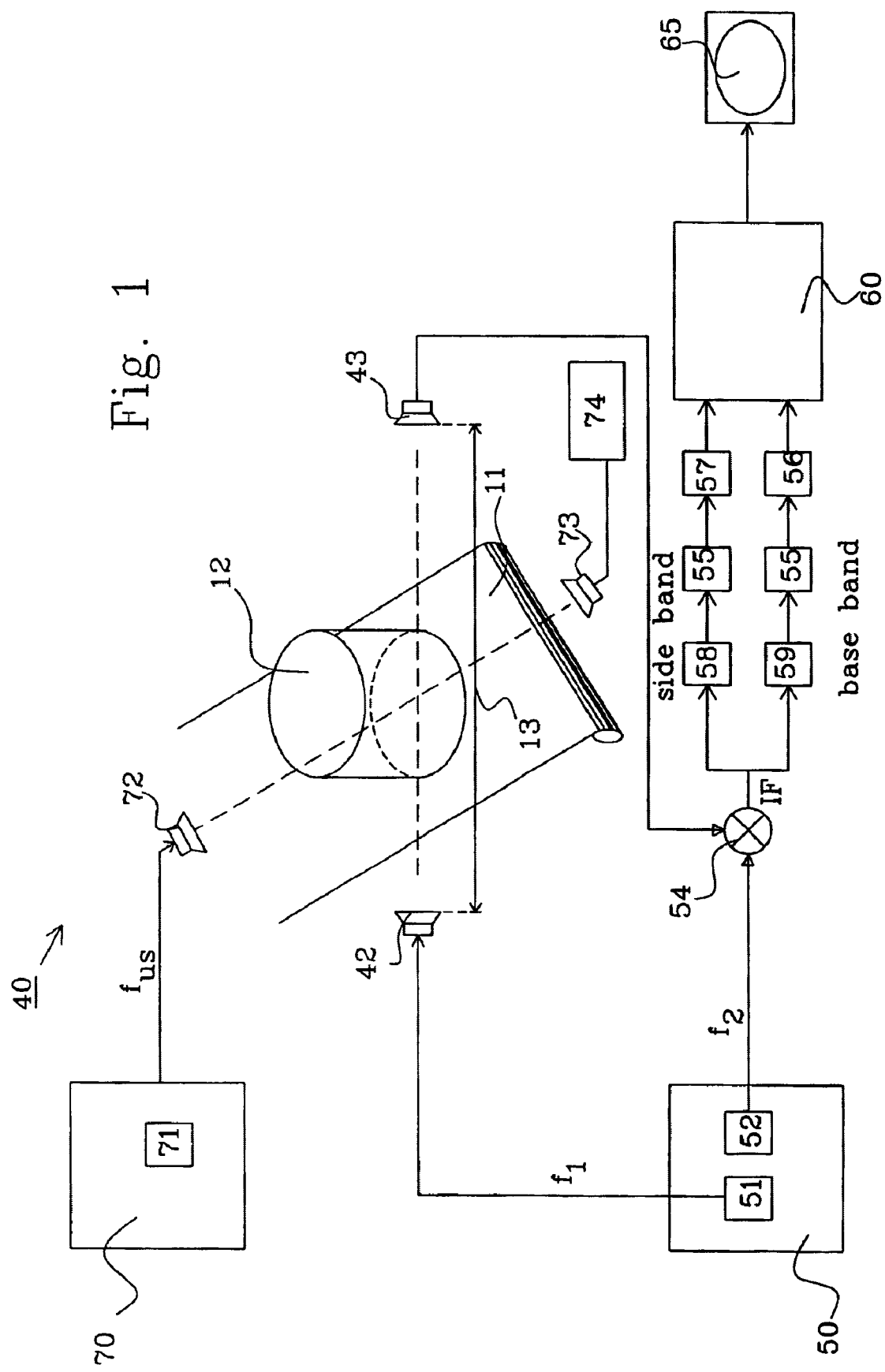
FIG. 1 shows a system according to the invention.

Prior to this invention there exist as tools for reconstructing the interior properties of materials (where diffraction and scattering are predominant) only microwave tomography ultrasound tomography.

In both cases, resolution is determined by the wavelength of the used radiation.

In this invention, ultrasound and microwave methods are combined. Object reconstruction can be done by pure microwave inverse scattering methods and by pure ultrasound tomography methods with their respective limitations. Here ultrasound is not used as an object reconstruction tool but as a tool to generate a density variation in the object to be investigated. This said density variation creates a change of phase and frequency in the transmitted microwave radiation that is used for object reconstruction. Therefore the available resolution of this method is determined by the resolution of the ultrasonic wave (smaller than a millimeter for typical medical ultrasound frequencies). The density readout is performed using microwave radiation (at a frequency where attenuation still allows reasonable penetration depths e.g. S, ISM5.8 or X band). This method avoids the fundamental difficulty of microwave tomography approaches that a millimeter resolution requires millimeter wavelengths. Unfortunately millimeter radiation is absorbed by most objects of interest within some wavelengths therefore not allowing any interior parameters to be extracted. In the above classification, this invention covers areas 1B, 2A and 2B. Such a method is not known prior to this invention.

The system described by this invention is preferably to be used in the food industry. In the food industry, it is often important to accurately control the temperature of food products. For example, when food products are to be freezed, it is important that the entire product is freezed. When it cannot be ensured that the entire product, e.g. a chicken fillet, has been freezed, one may have to discard products or deliver products with short shelf life. Therefore, there is a need for a non-destructed and non-contact control of the freezing of products. This problem may be solved by means of measuring the dielectric function and converting it to a distribution of temperature, as will be described in the following.

However, the system is by no means limited to this type of industry. Potential other applications are:

concrete hardening (construction industry)

glue hardening (airplane construction)

medical imaging (functional brain tomography, spinal tomography)

ground survey, tracking pipes and underground tubes save and rescue equipment (detecting persons under rubble)

mine sweeping (especially plastic mines in overgrown areas)

In the following the preferred embodiment is summarized. The modifications required to the geometry in order to adapt this method in the above other application areas are stall.

In the following a continuous wave (CW) microwave and pulse wave train ultrasound based system is described for sake of simplicity. The method described is not limited to this case. Other modulation schemes for both, electromagnetic waves and ultrasound waves such as amplitude modulation (AM), frequency modulation (FM) frequency modulated continuous wave (FMCW), pulse code modulation (PCM), phase modulation (PM) and wavelet based modulation techniques (WM) are applicable and are optimal for certain other applications.

FIG. 1 describes a apparatus 40 according to the invention. The system is placed close to a conveyor means 11, which transports the products under test 12 through the sensor measurement gap 13. The system 40 consists of a microwave part 50, an ultrasound part 70 and an evaluation unit 60. The system comprises in this embodiment two fixed-frequency microwave generators 51 and 52 and a fixed frequency ultrasound generator 71. The first microwave generator 51 has a first fixed microwave frequency $f_1$ (e.g. 5.818 GHz) and is coupled to at least one transmit antenna 42, and the second microwave generator 52 has a second fixed microwave frequency $f_2$ (e.g. 5.8 GHz) and is preferably coupled to a down converter 54, such as a mixer. The down converter shifts the transmitted microwave signal, which is collected by at least one receive antenna 43, and the received microwave signal from the second microwave generator 52 to a low intermediate frequency IF. This allows the microwave signal transmitted through the product under test 12 to be evaluated in amplitude and phase. It furthermore comprises a filter unit 59, an analog to digital converter ADC 55, a set of signal processors 56 and an evaluation processor 60 that contains necessary algorithms to control the system and to evaluate the data. The result is submitted to a display unit 65. The system 40 also comprises a set of transducers 72 (only one shown for sake of clarity), in addition to the transmit antenna 42 and receive antenna 43, all grouped around the measurement gap 13. The transducers emit an ultrasound signal having an ultrasound frequency $f_{US}$ (e.g. 4.5 MHz) through the product under test 12. This causes a density displacement traveling at ultrasound speed. At the same time a microwave signal from the first microwave generator 51 is emitted from the transmit antenna 42. This signal also travels through the product under test 12. The microwave signal exhibits damping and phase delay by traveling through the product leaving the microwave frequency unchanged. In those volumes of the product under test 12 where the ultrasound wave creates a density displacement, a part of the microwave signal is shifted in frequency and upper and lower sidebands are created. The transmitted microwave signal is collected using the microwave receive antenna 43. The received signal is down converted using the down converter unit 54. The low frequency signal is then filtered using a filter unit 59 and analog-digital converted using the ADC 55. The digital signal is evaluated using a receive signal processor 56. The receive signal processor converts the incoming digital signal to zero frequency using standard state-of-the-art digital filters.

The outcome of this filtering corresponds to the $S_{21}$ parameter, which is not shifted in frequency, between the transmit 42 and receive 43 antenna as well known to a person familiar with the art. In the above we refer to the receive antenna 43 as microwave port 2 and the transmit antenna 42 as the microwave port 1.

In the system described by this invention there is a second set of bandpass filter 58, another ADC 55 and a second digital signal processor 57 in parallel to the first signal path 59, 55, 56.

The bandpass filter 59 is tuned to the difference frequency between the both microwave generators 51 and 52, which in the present embodiment is 5.818 GHz–5.8 GHz=18 MHz. The second bandpass filter 57 is tuned to the difference frequency between the microwave generators (e.g. 18 MHz) added the center frequency (e.g. 4.5 MHz) of the ultrasound signal generator 71. Therefore this second digital signal processor path, containing 58, 55 and 57, converts the incoming signal to zero frequency that has been shifted in frequency by the ultrasound frequency. The measurement result is therefore limited to the cross section between the ultrasound and the microwave signal.

The IF bandwidth of the first 59, 55, 56 and second 58, 55, 57 digital receivers are chosen to be half the ultrasound frequency $f_{US}$ generated by the ultrasound generator 71. This is required to optimize the frequency shift by varying the ultrasound transducer phases.

During the first stage of obtaining an ultrasound metric of the product 12, an ultrasound receiver 73 has to be present which collects the ultrasound radiation emitted from the transducers 72 and evaluate the damping, $T_{56}$, and runtime as described in more detail below. In the above we refer to the ultrasound receiver 73 as microwave port 6 and the transducers 72 as the microwave port 5. The damping and runtime is evaluated in a ultrasound evaluation unit 74, but this may naturally be integrated in the evaluation unit 60.

Figure 2:
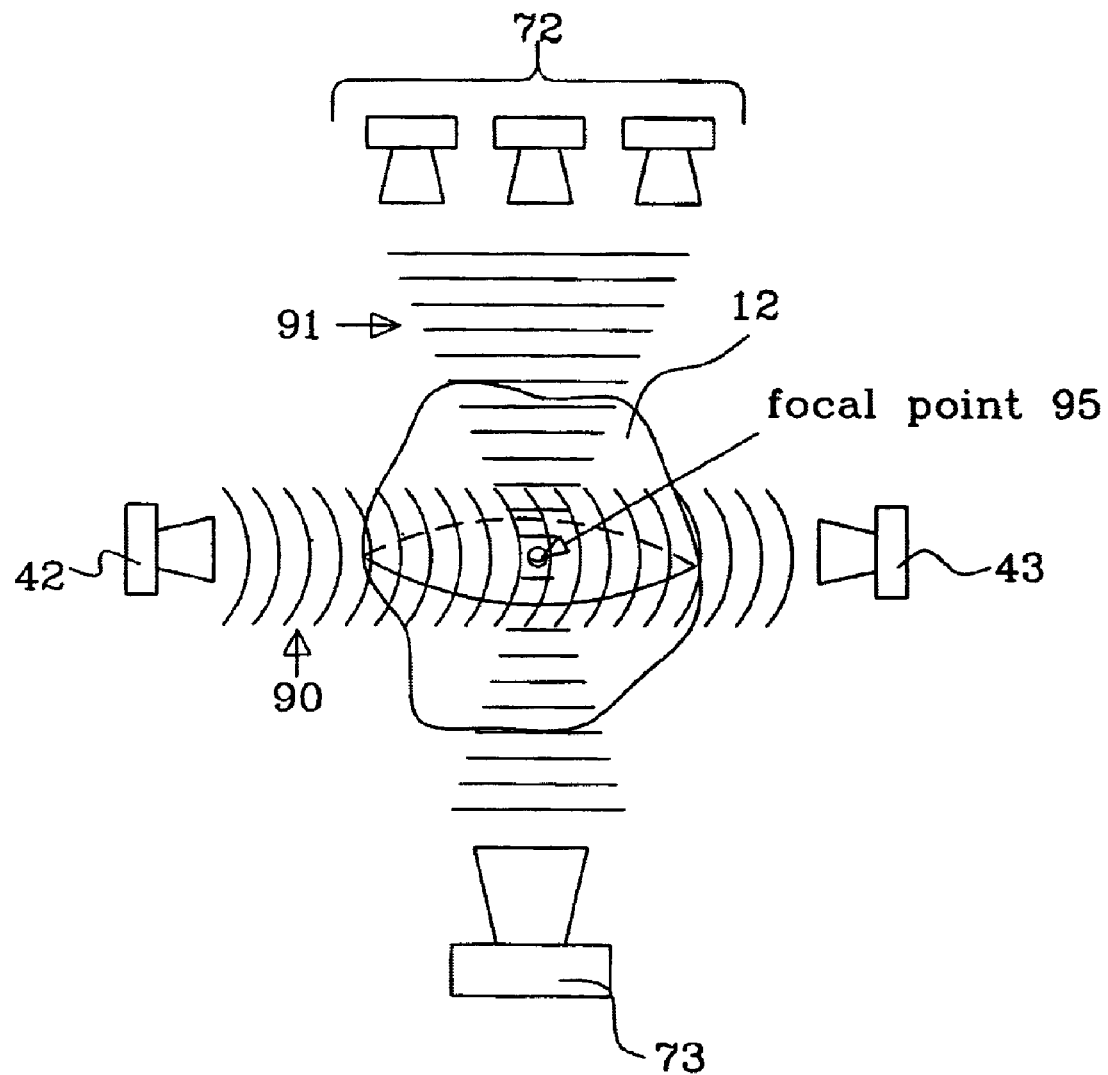
FIG. 2 illustrates the emitted radiation into a product under test.

FIG. 2 illustrates the emitted radiation into a product under test. The transducers 72 emit, in this example, an ultrasound pulse 91 through the product under test 12. This causes a density displacement traveling at ultrasound speed. At the same time a microwave signal 90 is emitted from the transmit antennas 42, travels through the product 12 and exhibit damping and phase delay with unchanged microwave frequency except in the area 95, where the ultrasound wave cause density displacement. In this area a part of the microwave signal is shifted in frequency, as described above, and upper and lower sidebands are created. The transmitted microwave signal 90 is collected using the receive antenna 43. The ultrasound wave 91 is collected in a receiver 73 during the process of obtaining the ultrasound metric which is used during the next stage of determining the spatial distribution of the dielectric function.

Figure 3:
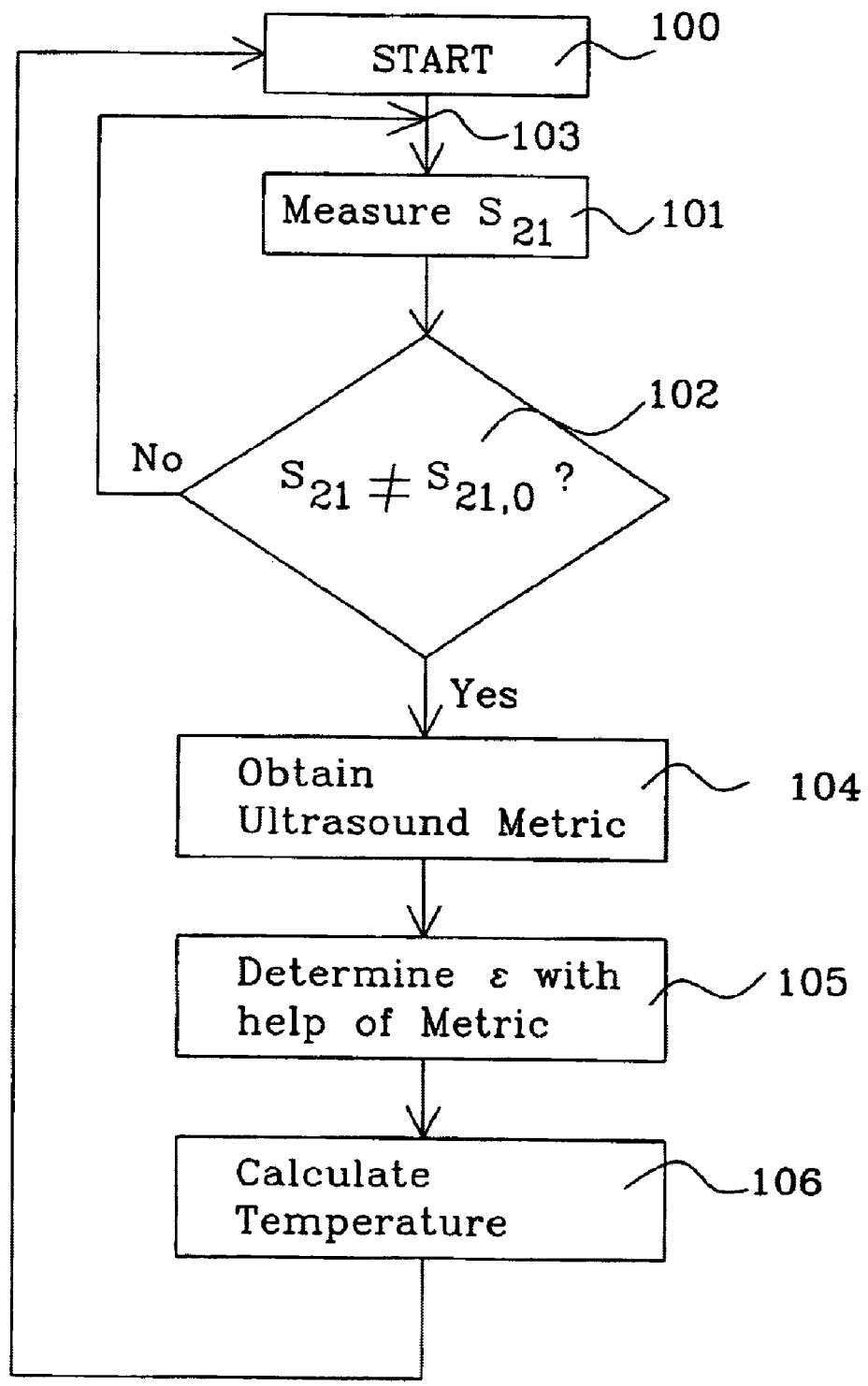
FIG. 3 shows a flow chart for determining a physical property, such as temperature, inside a product under test.

FIG. 3 show a flow chart describing the measurement principle according to the invention using a system as described in connection with FIG. 1.

Basically, the method of this invention is a microwave-ultrasound combination measurement method of the dielectric and the acousto-electric properties of matter where the resolution is inherited from the ultrasound wavelength.

The measurement procedure consists of three phases as described below.

Phase 1

Obtaining the Ultrasound Metric

In this phase a map of the local ultrasound runtime and damping properties are established which is henceforth referred to as the ultrasound metric.

By varying the phases between the ultrasound transducers 72 using a phase programming logic, any desired phase form of the ultrasound field can be generated. It is possible to control the phases of all ultrasound transducers in a way to focus the ultrasound power to a point with a geometrical size of the order of a half wavelength of the ultrasound wave. Focusing the ultrasound wave in the medium on the smallest possible volume causes the frequency displacement of the transmitted microwave signal to reach a maximum. Therefore, the phase of the ultrasound transducers is varied to optimize the microwave signal. Evaluating the delay time between the ultrasound pulse and the achieved maximum frequency shift allows determining at what distance from the antenna the focus point is located inside the product under test 2. This measurement is repeated for a set of points covering the whole product under test with a predetermined resolution.

As a result, a table comprising the phases to be chosen for each independent focus point and the location with respect to the antenna is obtained. At the same time, the strength of the maximum signal is obtained from each of these measurement points from all over the measurement object which allows to map the local ultrasound damping.

The local strength of the ultrasound signal is calculated by measuring runtimes and damping values between all ultrasound transducers. (Of course, any choice of phase is optimized by maximising the microwave signal for each point in this layer). Assuming these delay time and damping values for the layer of the product close to the transducers, the phase for the closest focus points are obtained.

Tuning the phases for transmission to focus the ultrasound power in one focus point and tuning the phases for reception to focus on another focus point, the runtime between the two focus points of the first layer is obtained.

Assuming these values to be valid around the focus points and also close to the next layer of points, phase and amplitude values for one after the other point of the next layer are obtained. (Of course, any choice of phase is optimized by maximizing the microwave signal for each point in any layer).

This process is repeated until the whole product under test is scanned.

The result is a table of the local damping of the ultrasound signal and the local phase delay of the ultrasound signal between all scanned focal points, the "ultrasound metric" together with the microwave signal strength for all the focal points.

The ultrasound metric may be obtained on a reference object, which is representative to the objects that are to be analysed. Thereafter, measurements may be made on such objects without the need of obtaining an ultrasound metric for each of the objects.

The metric by itself can also be considered as a substantial result of the invention and can be used as autonomous applications. Furthermore, metrics obtained on reference objects may be used as means to speed up measurements according to phase 1.

Phase 2:

Evaluating the Microwave Interaction

Based on the above generated ultrasound metric and the microwave response the acousto-electric interaction is obtained in a layer-by-layer wise starting from the layer closest to the microwave antennas. It is not required to proceed this analysis in a layer by layer way but it proves convenient for a subsequent 3D image processing to do so.

The strength of the microwave signal measured in each focal point is determined by the product of the (a) local strength of the ultrasound signal and (b) the compressibility and (c) the dielectric function of the material in the focus point.

Since the local strength of the ultrasound signal in all focal points is known from the metric, the interaction between the incident and the frequency-shifted transmitted microwave signal on the layer closest to the microwave antenna is obtained by applying a Green's function theorem resulting in the dielectric function at this focal point. No other point interaction than the interaction of this specific focal point is possible because the microwave sideband response must originate in the region where the ultrasound focus has extended during the measurement. Therefore the resolution of the method is given by the wave packet resolution of the ultrasound signal (down to 250 micrometers) and not by the microwave wavelength (of the order of several centimeters) in a non-disturbing way. Nevertheless the incident microwave signal is influenced by the neighboring elements on the way from the transmit antenna to the focal point and also on the way to the receive antenna. The microwave signal at the focal point depends on all the dielectric points in the product under test and is represented by a linear form in the contrasts and the incident field amplitudes. The field collected in the receive antenna is also described by a linear form containing all unknown contrasts. For each measurement, a bilinear form containing all unknown contrasts is obtained. For each measurement, a new equation is generated. Since there is an equation for each focal point, the equation system can be solved in a one-to-one way without iteration.

The result is a map of the acousto-electric and the dielectric properties of the product under test with the same underlying special structure as the ultrasound metric.

Phase 3:

Calculating the Acousto-Dielectric Properties

The ultrasound damping is not significantly temperature dependent. In contrast the ultrasound runtime and the dielectric function together with the compressibility of the product exhibit a strong temperature dependence.

The ratio between compressibility and dielectric function yields a function of temperature. Using the dielectric and acousto-electric maps, the temperature of the measurement object is obtained.

Further details of the third phase are described in connection with FIGS. 6 and 7a–7d.

Having described the three phases in detail, the measurement will now be further described with reference to FIG. 3.

The flow starts at step 100, which means that a microwave signal at the first frequency $\omega_{transmit}=2\pi f_1$ is sent out from the transmit antenna 42 and a microwave signal at a mix of frequencies $\omega_{transmit}$ and $\omega_{receive}$ is received at the receive antenna 43. A damping $S_{21}$ and a frequency offset 8 and a signal generation at the offset frequency $S'_{21}$ between the two signals is measured in step 101, and in the following step 102 the measured damping $S_{21}$ is compared to a previously recorded reference damping $S_{21,0}$, which corresponds to the measured damping with an empty measurement gap 13, i.e. no object under test 12 is present in the gap. If the measured damping is equal to the damping with no object under test present in the gap, the flow is fed back to point 103 and the damping is measured again in step 101.

When an object is introduced in the measurement gap 13 the flow continues to step 104 where an ultrasound metric is obtained. This step is described more closely in connection with FIG. 4.

The spatial dielectric properties of the object is thereafter measured and calculated using the metric obtained in step 104. This procedure is described in more detail in connection with FIG. 5.

When the dielectric properties of the object is determined other physical properties may be determined, step 106, such as temperature, water contents density, etc., using the spatial distribution of the dielectric properties (based on predetermined $\epsilon(T)$ models). Such models are known in the prior art, such as described in the published PCT-application WO02/18920, assigned to the present applicant.

Figure 4:
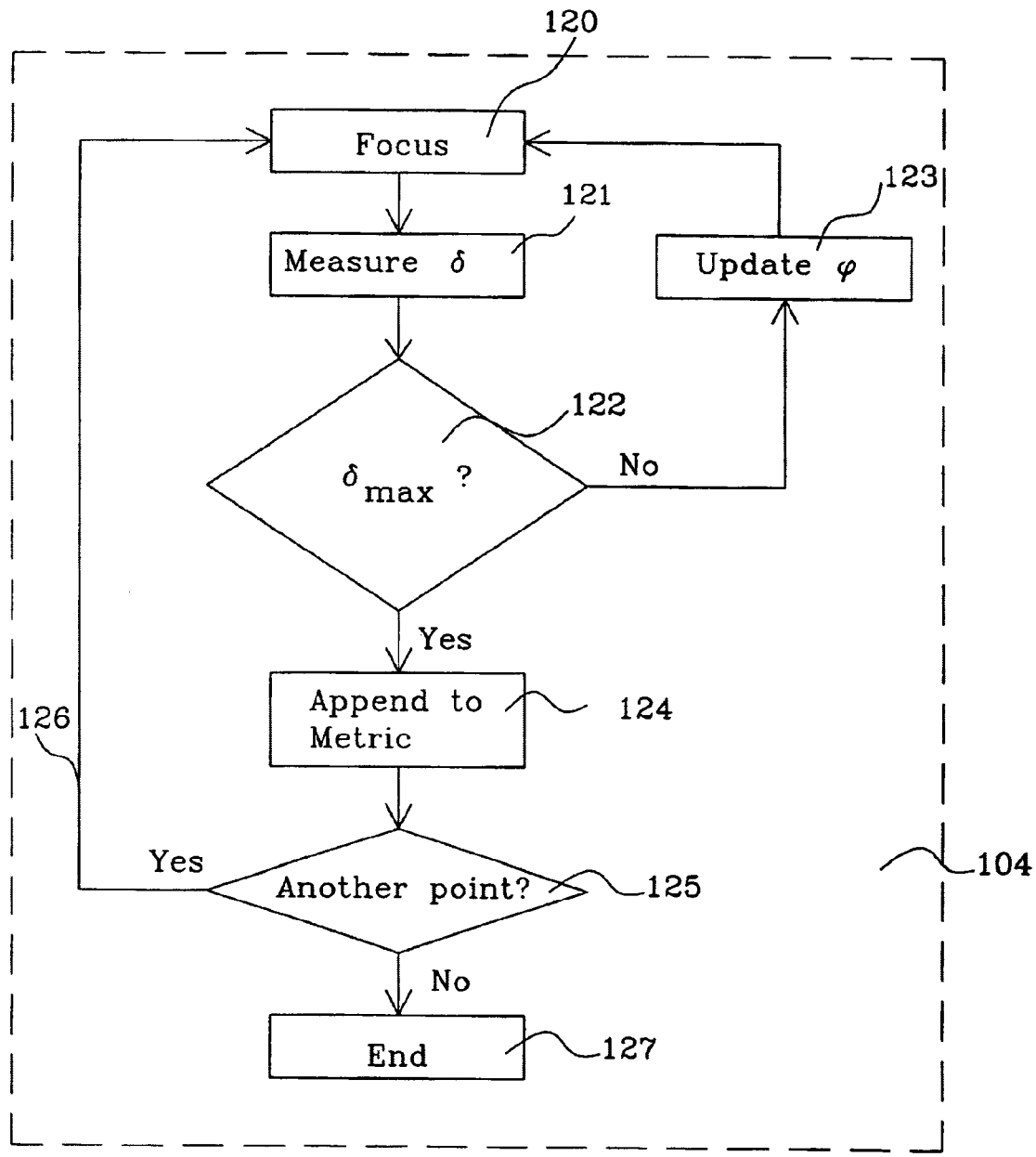
FIG. 4 shows a flow chart illustrating the process for obtaining an ultrasound metric.

FIG. 4 shows a flow chart disclosing the process of obtaining the ultrasound metric. The flow starts at step 120, where the ultrasound radiation is focused to a point in the object. The ultrasound will generate a signal in the sideband path, which corresponds to the frequency displacement measured by the microwave signal, denoted 5 and an acoust-electric efficiency signal, which is measured in step 121 and in step 122 a check is made to determine if the acousto-electric efficiency signal is at maximum, if not the flow is fed back through step 123, where the value of the phase of the ultrasound signal is updated, to step 120. The process is repeated until the maximum frequency displacement is obtained. When the flow continues to step 124, the phase of the ultrasound signal together with information regarding the position of the focal point as described above, is stored in a memory. In step 125 it is determined if there are another point that should be measured to obtain the ultrasound metric of the product under test 12. If not, the process for obtaining the metric ends in step 127, or the flow is fed back via line 126 to step 120.

Measurement of the Dielectric Function Based on a Known Ultrasound Metric (c.f. FIG. 4)

Figure 5A:
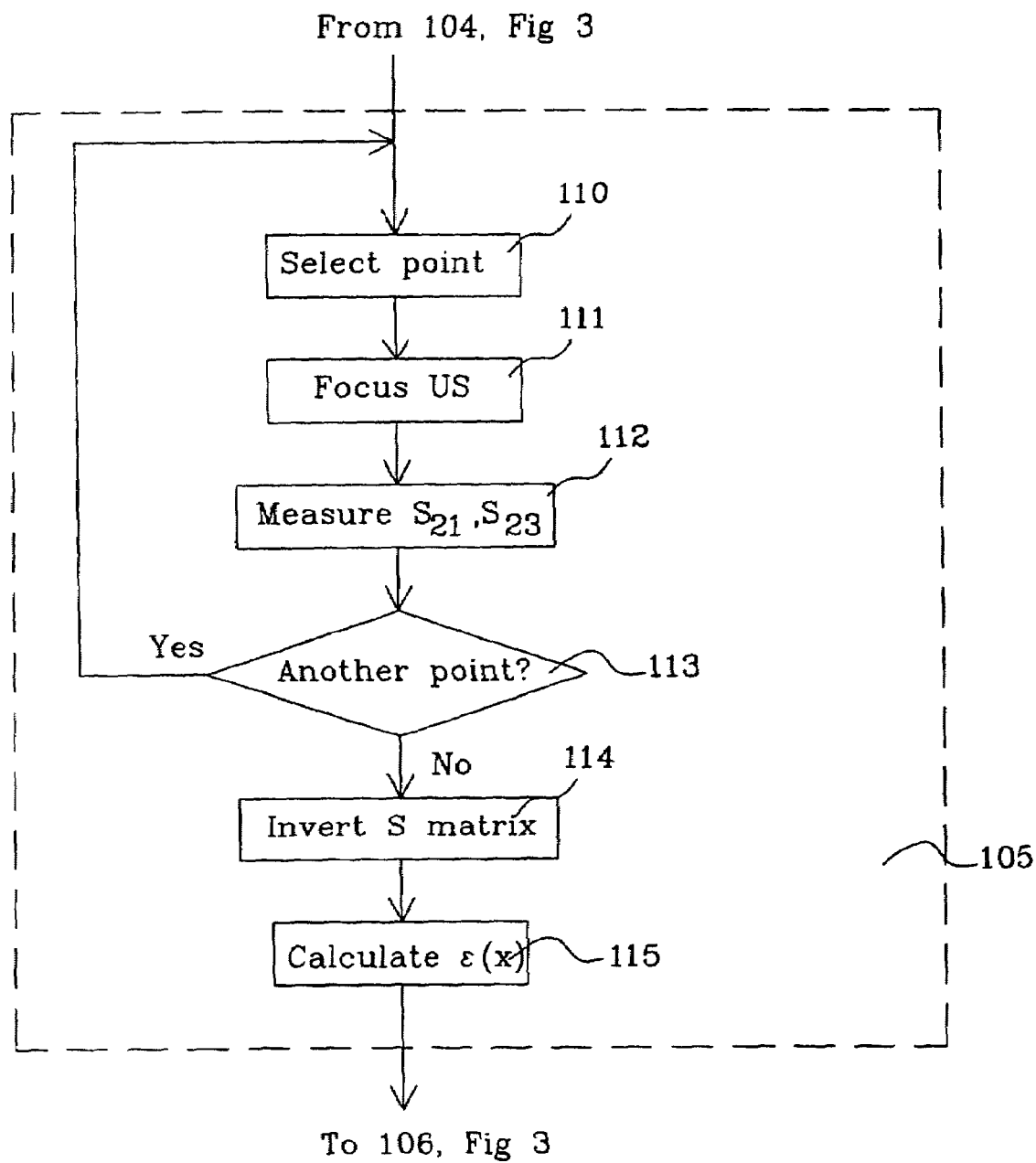
FIGS. 5a and 5b show flow charts illustrating two embodiments of the process for determining the spatial distribution of the dielectric function within a product under test.

FIG. 5a shows a first embodiment for determining the dielectric function in an object, such as a food product, to determine a physical property in the object, such as internal temperature without physically probing the object, during preparation of the object.

The flow starts in step 110, where a point in the object is selected. It is advantageous to select a point that has been used during the process of obtaining the ultrasound metric. The selected point corresponds to point 3 in equations 1–17.

The ultrasound radiation is thereafter focused on this point in step 111 and in step 112, the S-parameters $S_{31}$ and $S_{23}$ are measured, as described in more detail in connection with FIG. 6.

In step 113, a decision is made whether another point should be selected or not. If another point should be selected the flow is fed back to step 110, where a new point is selected before steps 111 and 112 are repeated. If not, the flow continues to step 114 where the matrix with the measured S-parameters is inverted to solve either $S_{31}$ for virtual receivers or $S_{32}$ for virtual transmitters.

The dielectric function $\epsilon(x)$ for each selected point x is thereafter calculated in step 115 using prior art algorithm. The temperature in the selected point is thereafter calculated as indicated by step 106 in FIG. 3.

Figure 5B:
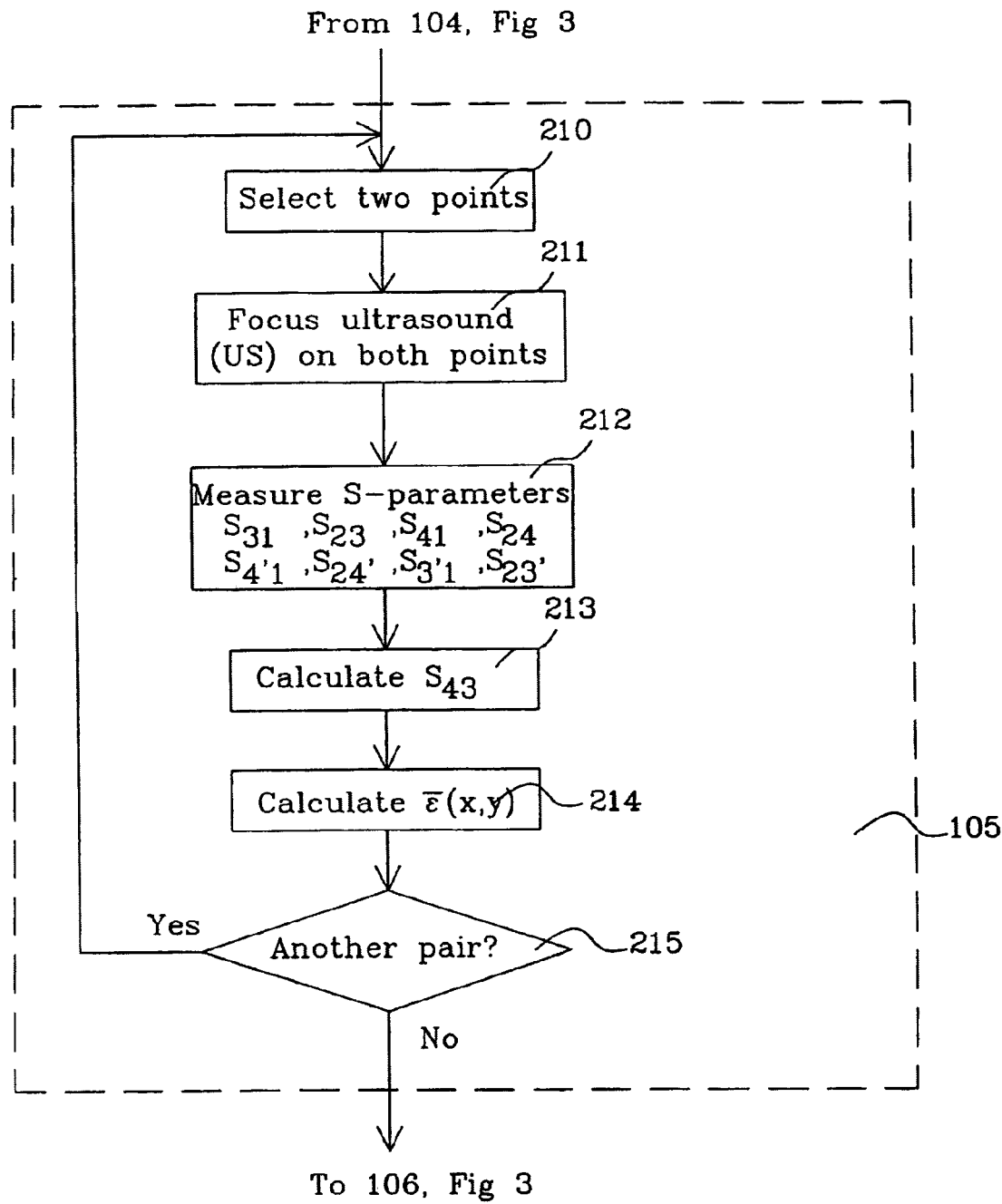

FIG. 5b shows a second embodiment for determining the dielectric function in an object, such as a food product, to determine a physical property between two locations in the object, such as material properties, e.g. the presence of a brain tumor, without physically probing the object.

The flow starts in step 210, where a pair of points in the object is selected. It is advantageous to select points that have been used during the process of obtaining the ultrasound metric. The selected points correspond to point 3 and 4 in equations 1–17.

The ultrasound radiation is thereafter focused on both points in step 211 and in step 212, the S-parameters $S_{31}$, $S_{23}$, $S_{41}$, $S_{24}$, $S_{4'1}$, $S_{24'}$, $S_{3'1}$ and $S_{23'}$ are measured, as described in more detail in connection with FIG. 7.

The S-parameter $S_{43}$, i.e. the damping between the selected points, is calculated in step 213. Point 3 acts as a virtual transmitter and point 4 functions as a virtual receiver in this embodiment.

The mean value of the dielectric function $\bar{\epsilon}(x,y)$ between the selected points x and y (i.e. points 3 and 4 in equations 1–7, is thereafter calculated in step 214.

In step 215, a decision is made whether another pair of points should be selected or not. If another pair of point should be selected the flow is fed back to step 210, where a new pair is selected before steps 211 to 214 are repeated. If not, the flow continues to step 106 in FIG. 3, where the desired physical properties are calculated.

First Use of the Invention

Figure 6:
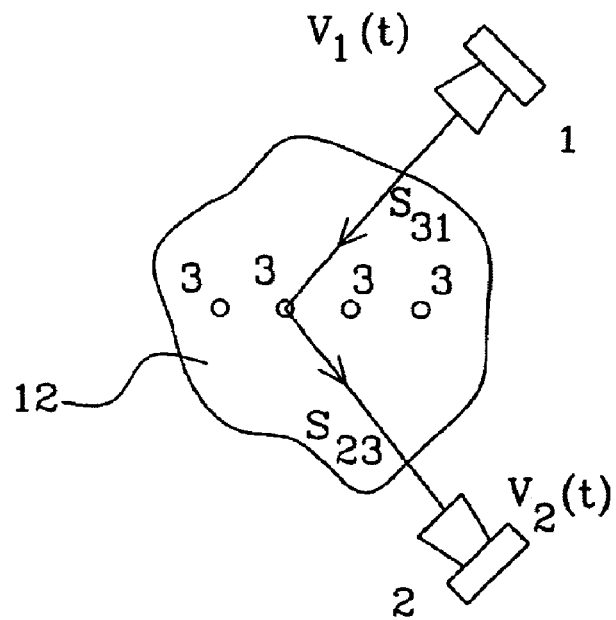
FIG. 6 shows a principal function of a first use of the present invention.

FIG. 6 shows a schematically the function of a first use of the present invention. If an ultrasound metric $u(x,t)$ is obtained for all points x within a product it is possible to calculate the dielectric constant in every point by applying the following steps:

1) Focus the ultrasound on one of the points 3. It is known that the ultrasound only affects the focal point concerning frequency shift of the microwave signal sent from the transmit antenna 1 to the receive antenna 2, thus generating a signal in the sidebands, i.e. microwave base frequency $(f_1) \pm$ ultrasound frequency $(f_{US})$).

2) Measure the signal strength in at least one of the side bands. If the signal strength in both side bands is measured, a more reliable result from the measurement is obtained. The signal strength measured in the receive antenna 2 may be expressed as:

$$V_2(t) = S_{21} \cdot V_1(t) = S_{23} \cdot \alpha_3 \cdot u_3(x,t) \cdot S_{31} \cdot V_1(t),$$

Where $S_{21}$ is the damping caused by the product 12 present in the measurement gap, $V_2(t)$ is the measured signal strength in the side band and $V_1(t)$ is the signal strength of the signal sent from the transmit antenna 1. $S_{23}$ is the damping between point 3 to the receive antenna 2, $\alpha_3$ is a factor that determines the efficiency in point 3 at which an ultrasound wave is converted into a microwave sideband signal (referred to as acousto-electric gain), $u_3(x,t)$ is the ultrasound metric in point 3 and $S_{31}$ is the damping between the transmit antenna 1 and point 3.

In a first approximation the efficiency $\alpha$ can be expressed as:

$$\alpha = \frac{\Delta \varepsilon}{y}$$

where $\Delta\epsilon$ is the change of dielectric constant due to the pressure wave cause by the ultrasound radiation, y. With the compression module $\kappa$, the relation $$\frac{\Delta \varepsilon}{\varepsilon - 1} = \kappa y$$

is established. The value of K is known to a skilled person in the arts and will not be discussed in more detail, 3) Repeat the process for all desired points, denoted 3 in FIG. 6, in the product 12.

4) Use all measurement data in an inverse scattering algorithm and calculate the spatial distribution of the dielectric function in the product.

If an object moves at a relative slow speed, and fulfilling the relationship below, in relation to the measurement apparatus, no compensation of the emitted ultrasound and microwave radiation needs to be taken into consideration.

$$v_{obj} \cdot t_{meas} < \frac{v_{US}}{f_{US}} = d_{Focal},$$

$v_{obj}$ is the speed of the objects movement in the measurement gap 13, $t_{meas}$ is the measurement time for the complete process, $v_{US}$ is the speed of ultrasound in the object, $f_{US}$ is the ultrasound frequency and $d_{focal}$ is the diameter of the focal point.

If the relative speed is high, the focusing of the ultrasound must include an adjustment of the ultrasound radiation, to maintain the focal point in the object during the measurement steps, to compensate for the movement. In addition $$\frac{v_{obj}}{v_{US}} << 1$$

to avoid Doppler shift.

Second Use of the Invention

FIGS. 7a–7d show a principal function of a second use of the present invention when calculating the dielectric constant between two points 3 and 4 in a product. A first point 3 may be considered to be a source and the second point 4 may be considered to be a receiver.

The principal function is very much the same as described in connection with FIG. 6, but with the exception that two upper and two lower sidebands are generated since two focal points 3 and 4 simultaneously generated by the ultrasound radiation. The first upper and lower side bands are the same as described in connection with FIG. 6, and the second upper and lower side band have the double ultrasound frequency, i.e. microwave base frequency $(f_1) \pm 2*$ultrasound frequency $(2f_{US})$. If the same ultrasound frequency is used for this purpose, it is possible to choose two different ultrasound frequencies to generate second order sideband. The apparatus described in connection with FIG. 1 needs in this example to be added with an extra sideband path adjusted for the second upper and lower sideband.

The following relationships can be established for point 3 and 4, each as a single virtual source:

$$V_2(t) = S_{23} \cdot \alpha_3 \cdot u_3(x,t) \cdot S_{31} \cdot V_1(t) \text{ (solid line)} \qquad 1$$

$$V_2(t) = S_{24} \cdot \alpha_4 \cdot u_4(x,t) \cdot S_{41} \cdot V_1(t) \text{ (dashed line)} \qquad 2$$

Figure 7A:
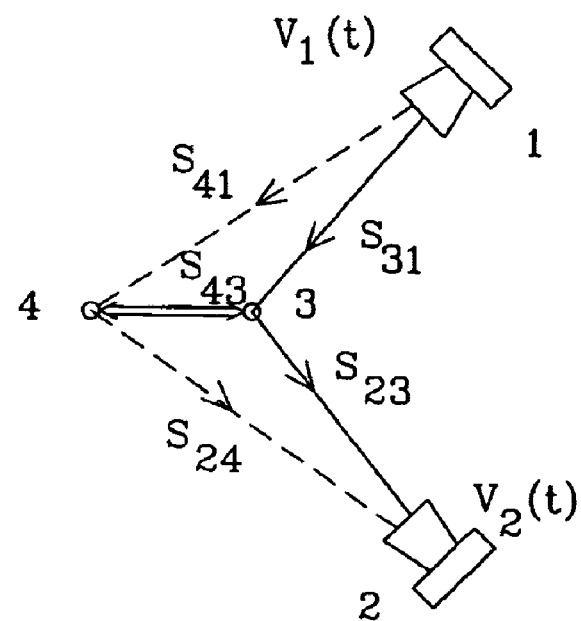
FIGS. 7a–7d show a principal function of a second use of the present invention.
Figure 7B:
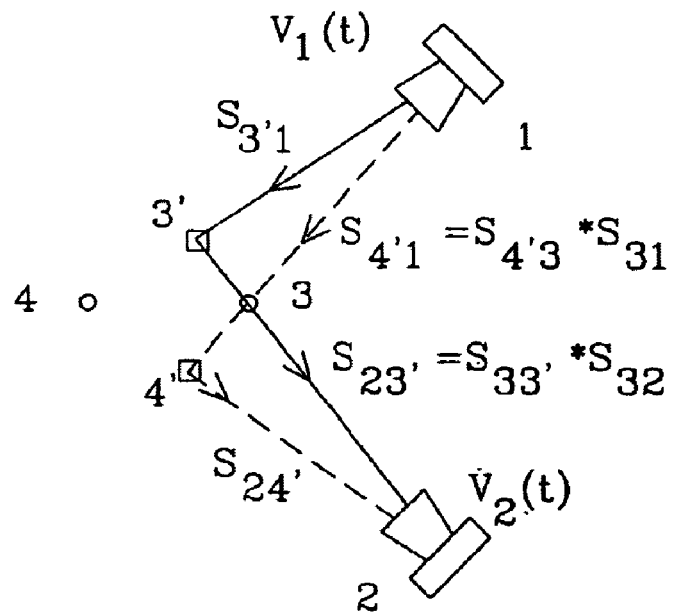

By displacing the focal point from 3 to 3' and the focal point from 4 to 4' according to FIG. 7b new relationships can be expressed:

$$V_2(t) = S_{23'} \cdot \alpha_{3'} \cdot u_{3'}(x,t) \cdot S_{3'1} \cdot V_1(t) \text{ (solid line)} \qquad 3$$

$$V_2(t) = S_{24'} \cdot \alpha_{4'} \cdot u_{4'}(x,t) \cdot S_{4'1} \cdot V_1(t) \text{ (dashed line)} \qquad 4$$

From FIG. 7a a relationship including the sought damping between point 3 and 4 may be expressed:

$$V_2(t) = S_{24} \cdot \alpha_4 \cdot u_4(x,t) \cdot S_{43} \cdot \alpha_3 \cdot u_3(x,t) \cdot S_{31} \cdot V_1(t) \text{ (double arrow 3=>4)} \qquad 5$$

$$V_2(t) = S_{23} \cdot \alpha_3 \cdot u_3(x,t) \cdot S_{34} \cdot \alpha_4 \cdot u_4(x,t) \cdot S_{41} \cdot V_1(t) \text{ (double arrow 4=>3)} \qquad 6$$

Equation 6 is not used in solving the 7×7 problem and is replaced by a suitable approximation, see equations 16 and 17.

Figure 7C:
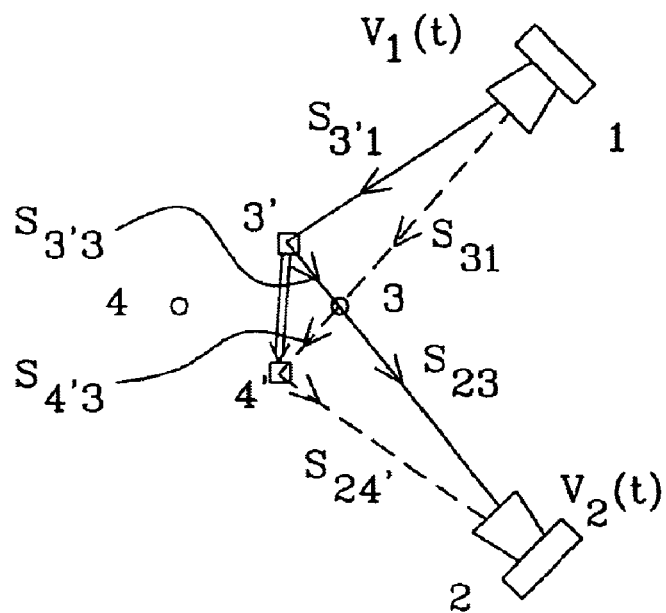

FIG. 7c illustrates the relationship of the double source corresponding to 3 and 4.

$$V_2(t) = S_{23} \cdot \alpha_3 \cdot u_3(x,t) \cdot S_{3'3} \cdot a_{3'} \cdot u_{3'}(x,t) \cdot S_{3'1} \cdot V_1(t) \text{ (solid line)} \qquad 7$$

$$V_2(t) = S_{24'} \cdot \alpha_{4'} u_{4'}(x,t) \cdot S_{4'3} \cdot \alpha_3 \cdot u_3(x,t) \cdot S_{31} \cdot V_1(t) \text{ (dashed line)} \qquad 8$$

The relationship between point 3' and 4' may be expressed:

$$V_2(t) = S_{24'} \cdot \alpha_{4'} u_{4'}(x,t) \cdot S_{4'3} \cdot \alpha_3 \cdot u_3(x,t) \cdot S_{3'1} \cdot V_1(t) \text{ (double arrow 3'=>4')} \qquad 9$$

$$V_2(t) = S_{23'} \cdot \alpha_{3'} u_{3'}(x,t) \cdot S_{3'4} \cdot \alpha_{4'} \cdot u_{4'}(x,t) \cdot S_{4'1} \cdot V_1(t) \text{ (double arrow 4'=>3')} \qquad 10$$

Equation 10 is not used in solving the 7×7 and 8×8 problem and is replaced by a suitable approximation, see equation 15 for the 8×8 problem and equations 16 and 17 for the 7×7 problem.

The following relationships are evident from FIGS. 7a–7c:

$$S_{41} = S_{43} \cdot S_{3'1} \qquad 11$$

$$S_{24} = S_{44'} \cdot S_{24'} \qquad 12$$

$$S_{23'} = S_{22'} \cdot S_{23} \qquad 13$$

$$S_{4'1} = S_{4'3} \cdot S_{31} \qquad 14$$

Figure 7D:
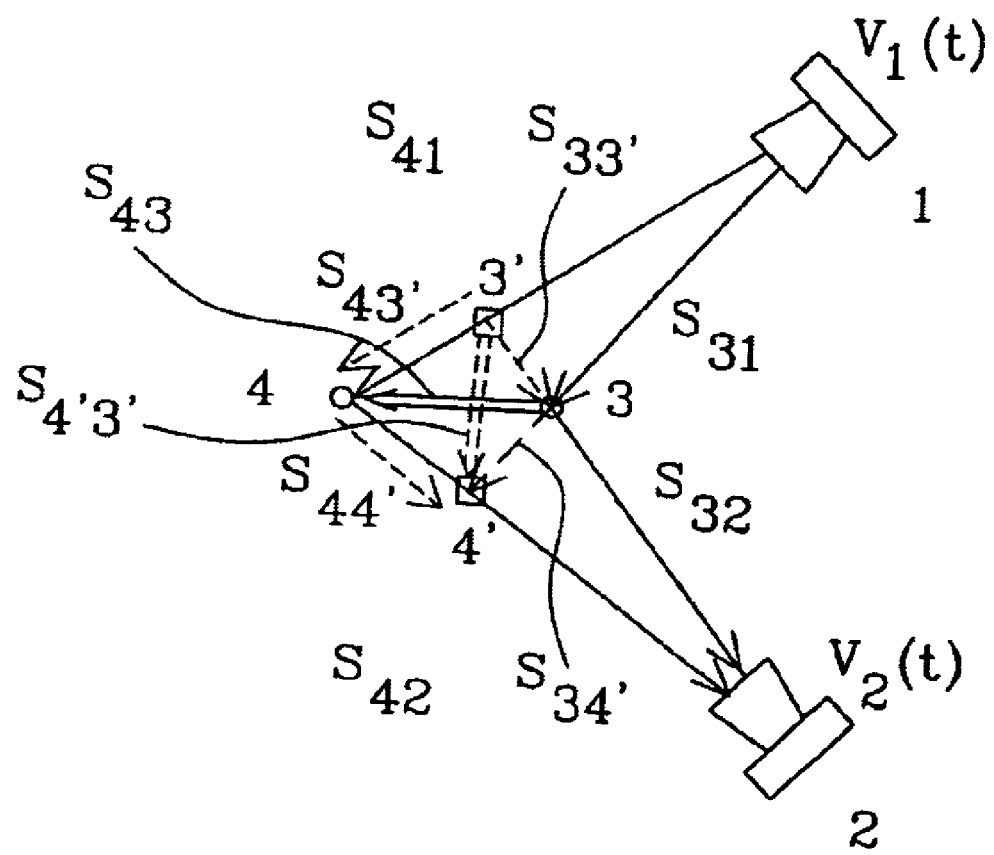

Equations 11–14 are used to eliminate S-parameters, which results in the S-parameters as illustrated in FIG. 7d. There is one S-parameter that is sought $S_{43}$ and one S-parameter that is completely uninteresting $S_{3'4'}$, together with several unknown S-parameters that require 10 equations to solve the problem, i.e. equations 1–10.

It is possible to reduce the number of equations needed to find the damping between point 3 and point 4 by applying a trick introduced by Zienkiewicz for Finite Elements. Equation 10 is not used and an approximation is used instead:

$$S_{4'3} \approx 1/2[S_{4'3} S_{33} + S_{4'4} S_{43'}] \qquad 15$$

It is even possible to reduce the number of equations needed to only 8 equations by applying Zienkiewicz tric twice, which eliminates the need of equations 6 and 10. The approximation used instead of the equations are:

$$S_{4'3} \approx 1/2[S_{4'3} S_{33} + S_{44} S_{43'}] \qquad 16$$

$$S_{43} \approx 1/2[S_{43} S_{33} + S_{44} S_{34'}] \qquad 17$$

The damping $S_{43}$ between point 3 and 4 and between point 3' and 4' can be calculated by turning the needed equations to logarithms, Equations 1 through 10 become a inhomogenous linear system of equations with as many unknowns as equations where a solution is always available as long as the analysis points are chosen properly. One has to solve the system for $S_{43}$ in order to obtain the microwave runtime between point 4 and point 3 illustrating the role of these points as "virtual probes".

The above described system uses a "virtual transmitter" (i.e. point 3) and a "virtual receiver" (i.e. point 4). One can easily place one of these point to coincide with a real transmit or receive antenna respectively arriving at the first usage of the invention. Placing both virtual probes at the place of the physical probe antennas will result in the traditional microwave measurement technique known prior to this invention.

Depending on the physical problem to be solved, one utilizes a single (virtual receiver or virtual transmitter) or both virtual probe concepts. It is also possible to use sets of probes (e.g. virtual probe arrays) to create a specific beam pattern generated/received by the virtual probes.

Different probe configurations may be used for applications as mine sweeping, material analysis, mineral exploration, medical applications etc.

Shorthand Mathematical Derivation of the Method:

Electromagnetic radiation is governed by Maxwell's equations where the vectorial electric field E is easily cast into a Helmholtz-form that is written in three dimensional space x and time t dependent coordinates as:

$$\Delta^2 E - \delta_0 \varepsilon_r \mu_0 \mu_r \frac{\partial}{\partial t^2} E = 0$$

Where $\Delta$ is the Laplace operator, $\varepsilon_0$ the dielectric constant of vacuum, $\varepsilon_r$ the local relative dielectric function of the material at a given location (being a 3×3 tensor), $\mu_0$ stands for the permeability of vacuum and $\mu_r$ for the local relative permeability of the material under test. In this shorthand derivation, $\mu_r$ is set to be the unit tensor 1 (3×3). To a skilled person it is obvious that a similar method can be derived by solving for $\varepsilon_r$ and $\mu_r$ simultaneously.

At the same time, ultrasonic waves with a tensorial 3×3 stress amplitude y and a local sound speed of the medium v can also be cast in a similar form $$\Delta^2 y - v \frac{\partial}{\partial t^2} y = 0$$

The solutions of both differential equations are performed taking the location of the radiation sources into account. Focusing on the key point of the process, any ultrasonic wave with a non-vanishing amplitude creates a stress in the material (being of compression or shear type). This stress is reflected by a local compression of the material: By this compression, the density of polarized charge is affected—as a known fact, any compression of a dielectric object changes the relative dielectric function tensor $\epsilon_r$ as:

$$\epsilon_r \approx \epsilon_{r0} + \alpha \cdot y$$

This relation creates a coupling between ultrasonic wave propagation and electromagnetic waves exploited in this invention. The strength of the interaction is determined by the acousto-optical interaction a being a 3×3×3 tensor. For a complete picture of the physics involved one has to mention that the above relation only holds for comparably small ultrasound waves where e.g. cavitation and other nonlinear effects can be neglected.

The complete system to be solved for electromagnetically is then given by:

$$\Delta^2 E(x,t) - \varepsilon_0 [\varepsilon_{r0} + \alpha \cdot y(x,t)] \mu_0 \mu_r \frac{\partial}{\partial t^2} E(x,t) = 0$$

To a person skilled in the art it is obvious that this type of differential equation becomes a convolution in frequency space $\omega$ when Fourier transform in time t is applied:

$$\Delta^2 E(x,\omega) + \omega^2 [\epsilon_{r0} + \alpha \cdot y(x,\omega)] \mu_0 \mu_r \oplus E(x,\omega) = 0$$

And where the circled times operator $E(x,\omega)$ denotes a frequency convolution integral (e.g. found in "Anleitung zum praktischen gebrauch der Laplace transformation" by G. Doetsch, 1988) that becomes in full form (omitting eventual normalization constants in front of the convolution integral):

$$[\Delta^2 + \omega^2 \varepsilon_0 \varepsilon_{r0} \mu_0 \mu_r] E(x,\omega) +$$
$$\alpha \cdot \omega^2 \varepsilon_0 \mu_0 \mu_r \lim_{Q \to \infty} \int_{\xi=-Q}^{+Q} y(x, \omega - \xi) E(x, \xi) d\xi = 0$$

Therefore assuming a single frequency ultrasound excitation and a single frequency microwave signal incident to the object, the received microwave signals contain a part in the incident microwave frequency but also sidebands at the difference and sum of ultrasound and microwave frequencies created by the convolution integral.

The above relation offers a whole new world to extract information from a microwave field—by properly phase—controlling the ultrasound and by using pulsed wave trains.

Single virtual probe

One applies the method to solve along a path involving a single virtual probe. This corresponds to either a virtual transmitter or a virtual receiver depending on what transmission parameter one solves the upcoming linear equation system that has been described above where all relations to either point 3 or 4 vanish. The wave propagation mechanisms are identical for this case. For the ideal (homogenous, boundary condition free) case, one arrives at the following propagation relations:

$$[\Delta^2 + \omega^2 \epsilon_0 \epsilon_r \mu_0 \mu_r] E(x,\omega) + \alpha \cdot \omega^2 \epsilon_0 \mu_0 \mu_r E(X, \omega - \xi) = 0$$

$$[\Delta^2 + (\omega - \xi)^2 \epsilon_0 \epsilon_r \mu_0 \mu_r] E(x, \omega - \xi) = qE(X, \omega - \xi)$$

Double Virtual Probe

In addition one can apply the method to solve along a path through two virtual probes. This corresponds to either a virtual transmitter or a virtual receiver depending on what transmission parameter one solves the upcoming 9×9 linear equation system that has been described above where all equations are present. For the ideal (homogenous, boundary condition free) case, one arrives at the following propagation relations $$[\Delta^2 + \omega^2 \epsilon_0 \epsilon_r \mu_0 \mu_r] E(x,\omega) + \alpha \cdot \omega^2 \epsilon_0 \mu_0 \mu_r E(X, \omega - \xi) = 0$$

$$[\Delta^2 + (\omega - \xi)^2 \epsilon_0 \epsilon_r \mu_0 \mu_r] E(x, \omega - \xi) = +qE(X, \omega - \xi)$$

$$[\Delta^2 + (\omega - \xi - \eta)^2 \epsilon_0 \epsilon_r \mu_0 \mu_r] E(x, \omega - \xi - \eta) = +q'qE(Y, \omega - \xi - \eta)$$

The first two equations denote the generation of a sideband at the analysis point X taking the role of a virtual transmitter. The third equation denotes the generation of a second sideband on top of the first by focussing at another analysis point Y which takes the role of a virtual receiver. The frequency offsets are denoted $\eta$ at point X and $\eta$ at point Y determined by the frequency of the ultrasound used to accomplish focusing. Please note that these may not be the same frequencies for both points X, Y in certain applications.

The first equation states the generation of a sideband at a predetermined location $\xi$ with the sideband offset x. The second equation states the propagation of the sideband through the whole object under test when a source with strength q is placed a position X. The method allows therefore to "probe" the object by synthesizing a microwave source at arbitrary positions inside the object. One measures then the radiation generated from this source when moving this source around.

What is claimed is:

1. An apparatus for determining a dielectric function in an object, said apparatus comprising:
   at least one transmit antenna for transmitting microwave radiation through said object,
   at least one receive antenna for receiving the transmitted microwave radiation,
   at least one ultrasound transmitter for emitting ultrasound radiation through said object to generate a density variation in the object,
   means to analyse the microwave radiation transmitted through the density variation to determine the acousto-electric interaction in the object, and
   means to calculate the dielectric function in the object from the acousto-electric interaction.

2. The apparatus according to claim 1, wherein said at least one transmit antenna is connected to a first microwave generator generating a transmit signal having a first fixed microwave frequency which is transmitted from said first antenna.

3. The apparatus according to claim 1, wherein apparatus further comprises a means to determine the attenuation comprising:
   a mixer producing an intermediate frequency signal by mixing the received transmitted microwave radiation from said receive antenna with a local oscillator signal having a second fixed microwave frequency, said local oscillator signal is generated by a second microwave generator, and an evaluation unit determining the acousto-electric interaction by evaluating phase and amplitude of the IF signal.

4. The apparatus according to claim 1, wherein said emitted microwave radiation and ultrasound radiation are arranged to be moved in relation to said object.

5. The apparatus according to claim 4, wherein said apparatus is stationary and the object is moved on a conveyor means.

6. The apparatus according to claim 4, wherein the apparatus is moved in relation to a stationary object.

7. The apparatus according to claim 1, wherein said ultrasound radiation is an ultrasound signal having a third fixed frequency, generated by an ultrasound generator.

8. The apparatus according to claim 1, wherein the apparatus further comprises at least one ultrasound receive antenna for receiving ultrasound radiation to determine an ultrasound runtime and damping mapping, referred to as metric for the object, which is used to determine the acousto-electric interaction in the object.

9. The apparatus according to claim 8, wherein the apparatus further comprises means to determine the phase of the ultrasound radiation for each focal point that is a part of the ultrasound metric.

10. A method for determining a dielectric function in an object comprising the steps of:
    transmitting microwave radiation through said object from at least one transmit antenna,
    receiving the transmitted microwave radiation in at least one receive antenna,
    emitting ultrasound radiation, from at least one ultrasound transmit antenna, through said object to generate a density variation in the object,
    analysing the microwave radiation transmitted through the density variation to determine the acousto-electric interaction in the object, and
    calculating the dielectric function in the object from the acousto-electric interaction.

11. The method according to claim 10, wherein the step of analysing the microwave radiation to determine the acousto-electric interaction in the object comprises the step of obtaining an ultrasound metric of the object.

12. The method according to claim 11, wherein the ultrasound metric is obtained by:

a) focusing emitted ultrasound radiation to a point in the object b) adjusting the phase of the ultrasound radiation while measuring an acousto-electric efficiency signal to obtain a maximum of the acousto-electric efficiency signal, c) storing the value of the phase together with position of the focal point in a memory, and d) repeating steps a)–c) until the metric for the object is completed.

13. The method according to claim 11, wherein the step of calculating the dielectric function in the object comprises the steps of:
    selecting at least one point inside the object,
    focusing the ultrasound on the point,
    determining the damping of the received transmitted microwave radiation, and
    determining the dielectric function using the ultrasound metric.

14. The method according to claim 11, wherein the step of calculating the dielectric function in the object comprises the steps of:
    selecting at least one pair of point inside the object,
    focusing the ultrasound on both points,
    determining the damping of the received transmitted microwave radiation for both points, and
    determining damping and the dielectric function between the two points using the ultrasound metric.

15. An apparatus for determining local distribution of temperature in a food product, said apparatus comprising:
    at least one transmit antenna for transmitting microwave radiation through said food product,
    at least one receive antenna for receiving the transmitted microwave radiation,
    at least one ultrasound transmit antenna for emitting ultrasound radiation through said food product to generate a density variation in the food product,
    means to analyse the microwave radiation transmitted through the density variation to determine the acousto-electric interaction ($\delta$) in the food product, and
    means to calculate the dielectric function in the food product from the acousto-electric interaction and to calculate the local distribution of temperature in the food product based on the calculated dielectric function.

* * * * *